Figure 1:
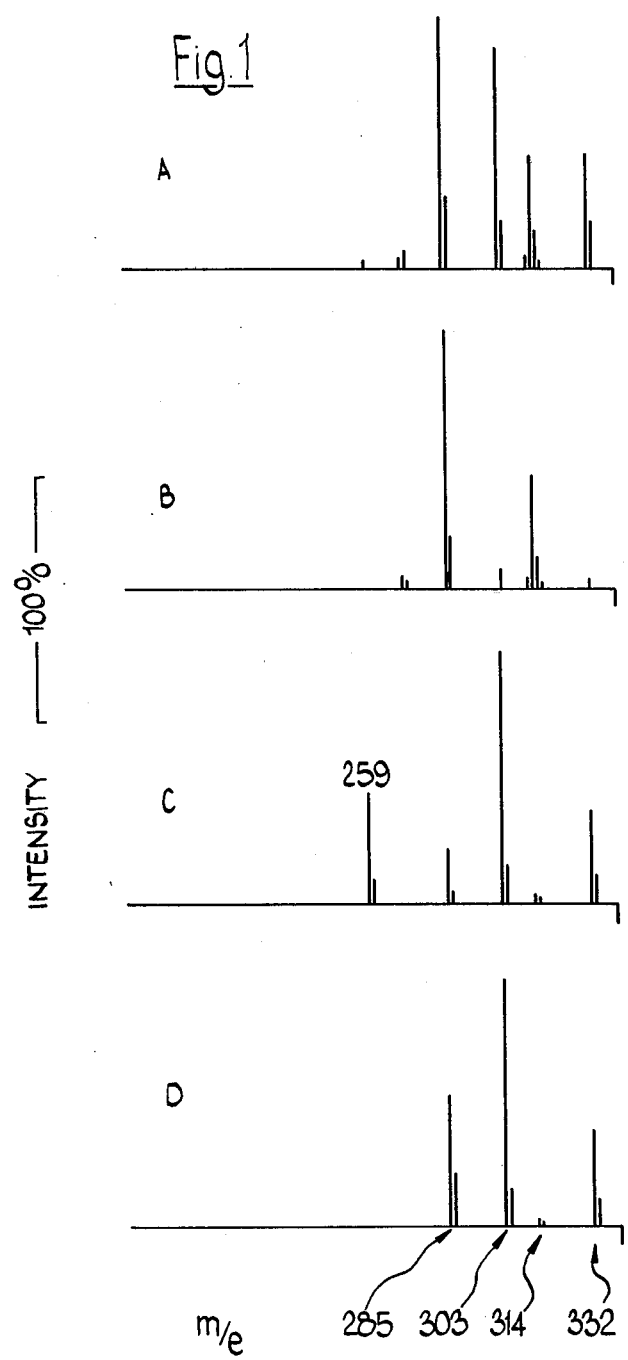

United States Patent [19]

Smith

[11] 4,269,854

[45] May 26, 1981

[54] 6,7,8,9-TETRAHYDRO-4H-NAPHTHO-[2,3-B]PYRAN-2-CARBOXYLIC ACIDS

[75] Inventor: Dennis A. Smith, Loughborough, England

[73] Assignee: Fisons Limited, Suffolk, England

[21] Appl. No.: 65,542

[22] Filed: Aug. 10, 1979

[30] Foreign Application Priority Data

Sep. 12, 1978 [GB] United Kingdom ............... 36428/78

[51] Int. Cl.³ .................... C07D 311/92; A61K 31/35
[52] U.S. Cl. ................................. 424/283; 260/345.2
[58] Field of Search ...................... 260/345.2; 424/283

[56] References Cited

U.S. PATENT DOCUMENTS 4,159,273  6/1979  Brown et al. .................... 260/345.2

OTHER PUBLICATIONS

Kano et al., J.C.S. Chem. Comm., 1979, pp. 414–415.
Nakai et al., Tetrahedron Letters, 1979, pp. 531–534.

*Primary Examiner*—Nicky Chan
*Attorney, Agent, or Firm*—Merriam, Marshall & Bicknell

[57] ABSTRACT

There are described compounds of formula I,

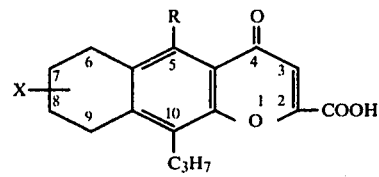

in which R is hydrogen, hydroxy or alkoxy C 1 to 6, and X is hydroxy, carbonyl oxygen or alkoxy C 1 to 6, and pharmaceutically acceptable derivatives thereof.

There are also described methods for making the compounds and pharmaceutical, e.g. anti-allergic, compositions containing them.

10 Claims, 3 Drawing Figures

6,7,8,9-TETRAHYDRO-4H-NAPHTHO-[2,3-B]PYRAN-2-CARBOXYLIC ACIDS

This invention relates to new compounds, methods for their preparation and compositions containing them.

According to our invention we provide compounds of formula I,

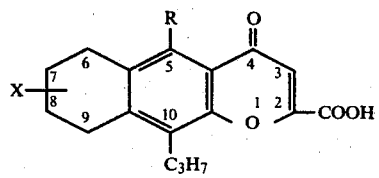

in which R is hydrogen, hydroxy, or alkoxy C 1 to 6, and

X is hydroxy, carbonyl oxygen or alkoxy C 1 to 6, and pharmaceutically acceptable derivatives thereof.

According to our invention we also provide a process for the production of a compound of formula I, or a pharmaceutically acceptable derivative thereof, which comprises, (a) cyclising a compound of formula II,

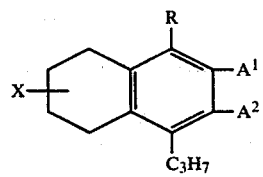

in which R and X are as defined above, $A^1$ represents —COCH$_2$COCOR", and $A_2$ represents —OM or a halogen atom, R" represents —OM, or a group which is hydrolysable thereto, and M represents hydrogen or an alkali metal, and if necessary or desired hydrolysing the group —COR", to a group —COOM, (b) selectively hydrolysing a compound of formula III,

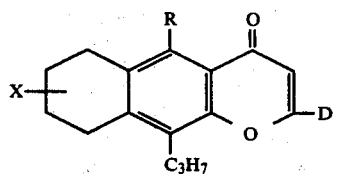

in which R and X are as defined above, and

D is a group which is hydrolysable to a —COOH group, or (c) producing a compound of formula I in which X is —OH by treating a corresponding compound of formula I in which X is —H, or a derivative thereof, with microsomal enzyme of the liver (or other suitable tissue) of a mammal, (d) producing a compound of formula I in which X is carbonyl oxygen, or a ester thereof, by selective oxidation of a corresponding compound of formula I, in which X is hydrogen, or an ester thereof, (e) producing a compound of formula I in which R is hydroxy, or an ester thereof, by selective hydrolysis of a corresponding compound of formula I in which R is alkoxy, or an ester thereof, (f) producing a compound of formula I in which X is hydroxy, or an ester thereof, by selective reduction of a corresponding compound of formula I in which X is carbonyl oxygen, or an ester thereof, and if necessary or desired hydrolysing the ester of the compound of formula I to a compound of formula I and/or converting the compound of formula I to a pharmaceutically acceptable derivative thereof.

When $A_2$ is a group —OM the cyclisation of process (a) may be carried out by heating, or under basic or neutral conditions. It is however preferred to carry out the cyclisation in the presence of an acid, e.g. hydrochloric acid, and in a solvent which is inert under the reaction conditions, e.g. ethanol. The reaction may be carried out at from about 20° to 150° C. The group —COR" is preferably an ester group, e.g. R" may be a lower alkoxy group. When $A_2$ is halogen the cyclisation may be carried out in a solvent which is inert under the reaction conditions, preferably a high boiling polar solvent, e.g. pyridine, dimethylformamide or hexamethylphosphoramide. The reaction is preferably carried out with the aid of a strong base, for example an alkali metal hydride, e.g. sodium hydride. The reaction is preferably carried out at a temperature of from about 80° to 200° C., in the absence of free oxygen, e.g. under an inert atmosphere such as nitrogen. When R is an —OH group the —OH may, if desired, be protected before the reaction and the protecting group removed after the reaction.

In process (b) the group D may be, for example an ester, acid halide, amide or a nitrile group, which may be hydrolysed to a —COOH group. The hydrolysis may be carried out using conventional techniques, for example under mildly basic conditions, e.g. using sodium carbonate, sodium hydroxide, sodium bicarbonate, or under acidic conditions, e.g. a mixture of aqueous dioxan and hydrochloric acid, or hydrogen bromide in acetic acid. Hydrolysis of the methyl ester may be effected by lithium iodide in pyridine. The hydrolysis may be carried out at a temperature of from about 25° to 120° C. depending on the compounds used.

In process (c) the mammal may be, for example a rat, rabbit, or man. The derivative of the carboxylic acid may be, for example a salt, e.g. an alkali metal salt, or an ester or an amide thereof. The microsomal enzyme may be used in vitro or in vivo. In in vivo use the pyran-2-carboxylic acid, or the derivative thereof, may be administered parenterally or orally to the mammal to be used. The animal's urine may then be collected over a period of several days and the product compound isolated from the urine using conventional techniques. In in vitro use the pyran-2-carboxylic acid, or the derivative thereof, is treated with a microsomal enzyme preparation which may be obtained by homogenising the liver in a suitable medium and centrifuging the homogenate to produce a supernatant liquid containing microsomal enzyme. The supernatant liquid together with the starting pyran-2-carboxylic acid, or the derivative thereof, and suitable nutrients, buffers, etc is then incubated for a suitable period and the product compound isolated from the reaction mixture using conventional techniques. When using in vitro procedures it is preferred that the animal be pretreated for a suitable period with a microsomal enzyme inducing compound, e.g. phenobarbitone.

In process (d) the selective oxidising agent may be for example chromium trioxide and the reaction may be carried out in a solvent which is inert under the reaction conditions, e.g. aqueous acetone. The reaction may be carried out at a temperature of from about 20° to 70° C.

In process (e) the selective hydrolysis may be carried out with acid optionally in a solvent which is inert under the reaction conditions. Thus the hydrolysis may be carried out using hydrogen bromide or formic acid in for example water, glacial acetic acid or trifluoroacetic acid at a temperature of from 0° C. to the boiling point of the solvent used.

In process (f) the selective reduction may be carried out using a metal hydride, for example a borohydride such as sodium borohydride. The reaction may be carried out in a suitable solvent, for example water, bis(2-methoxyethyl)ether or a mixture thereof, and may conveniently be carried out at a temperature of from about 0° to 40° C. Alternatively the reduction may be carried out using hydrogen and a catalyst, e.g. palladium on carbon. The catalytic reduction may be carried out in a suitable solvent, e.g. ethanol, at a temperature of from about 20° to 100° C. The catalytic reduction may be carried out at greater than atmospheric pressure, e.g. 1 to 50 atmospheres.

The compounds of formula II, in which $A^1$ and $A^2$ represent the groups —COCH$_2$COCOR″ and —OM or halogen, may be made by reacting a compound of formula V,

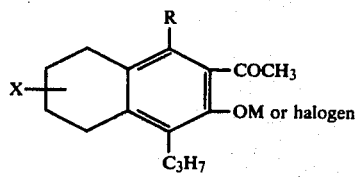

V or a protected, e.g. benzyl, derivative thereof,
in which M, R and X are as defined above, with a compound of formula VI,

      VI in which R″ is as defined above,
  R′ is a suitable leaving group, e.g. an alkoxy, halo, amino, alkylamino, substituted amino (e.g. an arylsulphonylamino group) or substituted alkylamino group, reactive with the carbanion of the —COCH$_3$ group of the compound of formula V, and
  each Z is carbonyl oxygen atom, or one Z may represent two halogen atoms and the other a carbonyl oxygen atom,
and if necessary hydrolysing the resulting compound to a compound of formula II. The preferred compounds of formula VI are dialkyl oxalates, e.g. diethyl oxalate.

The compounds of formula III may be made in a manner analogous to process (a) using a starting material of formula VII,

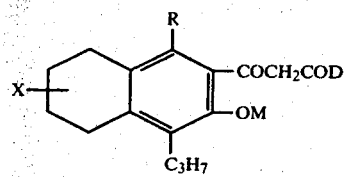 VII or a protected, e.g. benzyl, derivative thereof,
in which M, D, X and R are as defined above.

Compounds of formula III may also be made from known compounds by processes analogous to processes (d), (e) or (f).

The compounds of formula VII may be made from known compounds in a manner analogous to that described above for the preparation of the corresponding compounds of formula II, using a compound of formula R′COD in which R′ and D are as defined above, in place of the compound of formula VI.

Alternatively the compounds of formula III may, for example in the case of the acid halide, the amide and the nitrile, be made from compounds of formula I using conventional techniques, e.g. reaction of an ester of the compound of formula I with ammonia to produce the amide, followed by dehydration of the amide to form the nitrile.

The starting materials for processes (c) and (d) are either known or may be made from known compounds using techniques known per se. When X is carbonyl oxygen the position of the carbonyl oxygen may be changed by known ketone transposition techniques.

The compounds of formula I and the intermediates therefore may be isolated from their reaction mixtures using conventional techniques.

Pharmaceutically acceptable derivatives of the compounds of formula I include pharmaceutically acceptable salts, esters and amides of the 2-carboxylic acid group. Suitable salts include ammonium, alkali metal (e.g. sodium, potassium and lithium) and alkaline earth metal salts (e.g. calcium or magnesium), and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, or with simple monocyclic nitrogen heterocyclic compounds, e.g. piperidine or morpholine. Suitable esters include simple lower alkyl esters, e.g. the ethyl ester, esters derived from alcohols containing basic groups, e.g. di-lower alkyl amino substituted alkanols such as the β-(diethylamino)ethyl ester, and acyloxy alkyl esters, e.g. a lower acyloxy-lower alkyl ester such as the pivaloyloxymethyl ester, or a bis-ester derived from a di-hydroxy compound, e.g. a di(hydroxy-lower alkyl) ether, e.g. the bis-2-oxapropan-1,3-diyl ester. The pharmaceutically acceptable acid addition salts of the basic esters, e.g. the hydrochloride, the hydrobromide, the oxalate, the maleate or the fumarate may also be used. The esters may be made by conventional techniques, e.g. esterification, transesterification or reaction of the acid, or a salt thereof, with an appropriate compound containing a good leaving group. The amides may be, for example, unsubstituted or mono- or di- C 1 to 6 alkyl amides and may be made by conventional techniques, e.g. reaction of an ester of the corresponding acid with ammonia or an appropriate amine.

The compounds of formula I and pharmaceutically acceptable derivatives thereof are useful because they possess pharmacological activity in animals; in particular they are useful because they inhibit the release and/or action of pharmacological mediators which result from the in vivo combination of certain types of antibody and specific antigen e.g. the combination of reaginic antibody with specific antigen (see Example 27 of British Patent Specification No. 1,292,601). In man, both subjective and objective changes which result from the inhalation of specific antigen by sensitised subjects are inhibited by prior administration of the new compounds. Thus the new compounds are indicated for use in the treatment of asthma, e.g. allergic asthma. The new compounds are also indicated for use in the treatment of so-called 'intrinsic' asthma (in which no sensitivity to extrinsic antigen can be demonstrated). The new compounds may also be of value in the treatment of other conditions in which antigen-antibody reactions are responsible for disease, for example, hay fever; certain eye conditions, e.g. trachoma; alimentary allergy, e.g. urticaria and atopic eczema; and gastrointestinal allergy, especially in children, e.g. milk allergy.

The compounds of formula I, and the pharmaceutically acceptable derivatives thereof are also useful in the treatment or prevention of a condition, in a mammal, e.g. man, cats, dogs and horses, which condition involves skin mast cells and/or delayed (cellular) hypersensitivity reactions. Specific conditions in man and other animals which may be treated include contact dermatitis to a specific allergen, e.g. nickel, chromates, synthetic resins, applied medicaments and other chemicals (Rook A., Wilkinson DS and Ebling FJS 1972 Textbook of Dermatology 2nd Edition Blackwell, Oxford Chapters 14 and 15). Other conditions which may be treated are those having as a component a delayed (cellular) hypersensitivity, for example autoallergic conditions, in particular thyroiditis, glomerular nephritis, adrenalitis, encephalomyelitis (post rabies vaccination), systemic lupus erythrematosis, rheumatoid arthritis, myasthena gravis, polymyositis, ulcerative colitis, Crohn's disease, pemphigus, homograft rejection following the transplantation of tissues and organs; certain infectious diseases, in particular tuberculosis, brucellosis, staphylococcal disease, streptococcal disease and delayed allergy to toxins and vaccines. (Clinical Aspects of Immunology, (3rd Edition 1975), Eds P G H Gell, P R A Coombs, P J Lachmann, Chaps 25, 28 and 35). Dermatoses which may be treated include contact sensitivity, e.g. to chromium, nickel or an antibiotic, eczemas, drug eruptions, psoriasis, dermatitis herpetiformis, atopic dermatitis, apthous ulcers, Behcet's syndrome, pemphigus, urticaria, urticaria pigmentosa, the ulcers of Crohn's disease, pyoderma gangrenosum and chronic skin ulcers, notably those affecting man in tropical climates.

For the above mentioned uses the dosage administered will, of course, vary with the compound employed, the mode of administration and the treatment desired. However, in general, satisfactory results are obtained when the compounds are administered at a dosage of from 0.1 to 50 mg per kg of animal body weight in the test set out in Example 27 of British Patent Specification No. 1,292,601. For man the indicated total daily dosage is in the range of from 1 mg to 3,500 mg preferably from 1 mg to 3,000 mg and more preferably from 1 mg to 600 mg, which may be administered in divided doses from 1 to 6 times a day or in sustained release form. Thus unit dosage forms suitable for administration (e.g. by inhalation or oesophageally) comprise from 0.17 mg to 600 mg, preferably 0.17 mg to 500 mg and more preferably from 0.17 mg to 100 mg of the compound preferably admixed with a solid or liquid pharmaceutically acceptable diluent, carrier or adjuvant.

The compounds of formula I, and pharmaceutically acceptable derivatives thereof have the advantage that they are more efficacious in certain pharmacological models, e.g. of allergic conditions, or have less toxic side effects, e.g. in the disruption of cells, than compounds of similar structure to the compounds of formula I.

We prefer those compounds of formula I in which X is —OH and is preferably in the 7-position. We also prefer those compounds in which R is —OH. When R or X is alkoxy we prefer it to be methoxy.

According to our invention we also provide a pharmaceutical composition comprising (preferably less than 80%, and more preferably less than 50% by weight) of a compound of formula I, or a pharmaceutically acceptable derivative thereof, in combination with a pharmaceutically acceptable adjuvant, diluent or carrier. Examples of suitable adjuvants, diluents or carriers are: for tablets capsules and dragées; microcrystalline cellulose, calcium phosphate, diatomaceous earth, a sugar such as lactose, dextrose or mannitol, talc, stearic acid, starch, sodium bicarbonate and/or gelatin; for suppositories, natural or hardened oils or waxes; for inhalation compositions, coarse lactose; and for topical formulations, e.g. ointments, creams etc, solvents, fats waxes etc. The compound of formula I, or the pharmaceutically acceptable derivative thereof, when solid is preferably in a form having a mass median diameter of from 0.01 to 10 microns. The compositions may also contain suitable preserving, stabilising and wetting agents, solubilizers, sweetening and colouring agents and flavourings. The compositions may, if desired, be formulated in sustained release form. We prefer compositions which are designed to be taken oesophageally and to release their contents in the gastrointestinal tract, or which are designed to be administered topically to the skin.

Certain of the compounds of formula I are asymetric and may therefore exist in the form of two (or more) optical isomers or a racemic or other mixture of such isomers. The various optical isomers may be resolved, wholly or partially, using conventional techniques, e.g formulation of a salt with an optically active base, e.g. cinchonidine, fractional crystallisation of the salt and subsequent regeneration of the free acid.

The invention is illustrated, but in no way limited by the following Examples, in which the temperatures are in °C.

EXAMPLE 1

5,6-Dihydroxy-6,7,8,9-tetrahydro-4-oxo-10-propyl-4H-naphtho-[2,3-b]-pyran-2-carboxylic acid—B 5,7-Dihydroxy-6,7,8,9-tetrahydro-4-oxo-10-propyl-4H-naphtho-[2,3-b]pyran-2-carboxylic acid—C 5,8-Dihydroxy-6,7,8,9-tetrahydro-4-oxo-10-propyl-4H-naphtho-[2,3-b]-pyran-2-carboxylic acid—D 5,9-Dihydroxy-6,7,8,9-tetrahydro-4-oxo-10-propyl-4H-naphtho-[2,3-b]-pyran-2-carboxylic acid—A Three female Dutch rabbits (each weighing 2 kg) were dosed orally with 600 mg of 6,7,8,9-tetrahydro-5-hydroxy-4-oxo-10-propyl-4H-naphtho[2,3-b]pyran-2- carboxylic acid sodium salt over a period of 3 days. The urine was collected each day. The pH was adjusted to pH 1 and the urine was then extracted with diethyl ether. Most of the ether was evaporated and the residue was applied to silica gel preparative thin layer chromatography plates. Development with ether: chloroform: formic acid (2:7:1) separates the metabolites into the three main bands.

The bands are separated and eluted from the silica gel with 2% sodium bicarbonate solution. The eluates are acidified and extracted into ether. The partially pure metabolites are then esterified with an ethereal solution of diazomethane. The methyl esters formed are then rechromatographed on silica gel plates using chloroform/ether 7:2 as developing solvent. The esters are then purified finally by further chromatography using ether/petroleum ether 2:1 as developing solvent.

The main product of the chromatography was shown to be title compound C. The structure of the product compounds was elucidated by mass spectral measurements and by nuclear magnetic resonnance and infra red spectroscopy.

The compounds have the following melting points:
A = 189°–190° C.
B = 108°–109° C.
C = 125°–132° C.
D = 120°–126° C.

Figure 2:
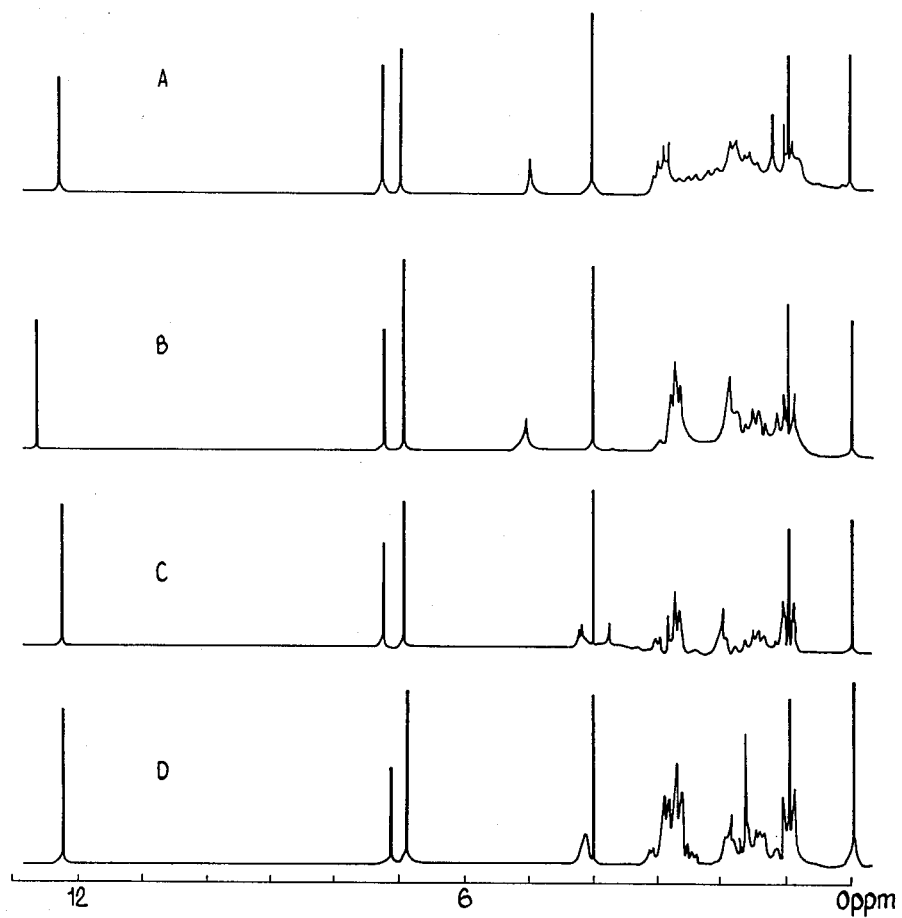
Figure 3:
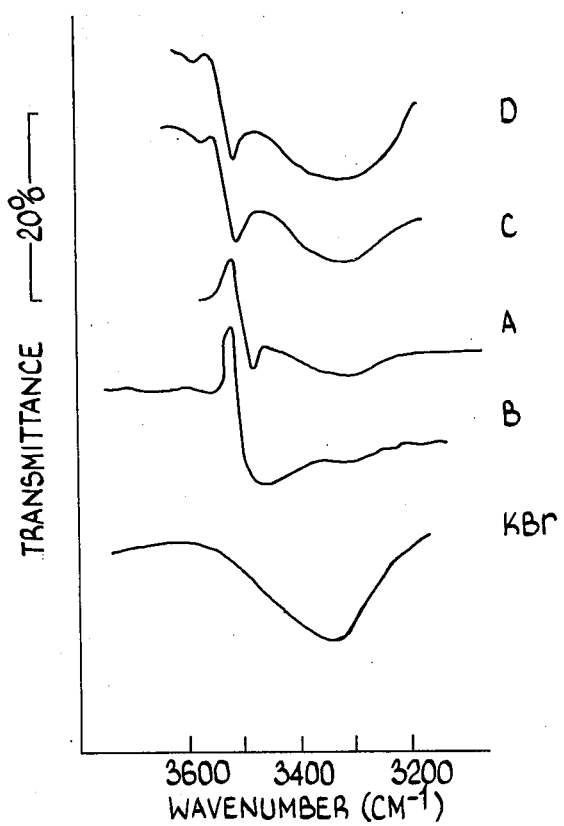

The mass spectra of the compounds are shown in FIG. 1, the nuclear magnetic resonnance spectra in FIG. 2 and the infra red spectra in FIG. 3.

EXAMPLE 2

5,7-Dihydroxy-6,7,8,9-tetrahydro-4-oxo-10-propyl-4H-naphtho-[2,3-b]pyran-2-carboxylic acid The liver from a freshly killed animal (rat or rabbit) was homogenised in three volumes of ice-cold 1.15% potassium chloride solution in a Potter-Elvehjem Glass homogeniser with a Teflon pestle. Subsequent centrifugation in a refrigerated centrifuge at 10,000 g for ten minutes gave a supernatant fraction which was used as a source of microsomal enzyme.

A mixture of 5 parts 6,7,8,9-tetrahydro-5-hydroxy-4-oxo-10-propyl-4H-naphtho[2,3-b]pyran-2-carboxylic acid sodium salt, 4 parts of 25% w/v supernatant liver fraction, 10 parts of phosphate buffer pH 7.4, one part of nicotinamide adenine dinucleotide phosphate and one part of glucose-6-phosphate was incubated in a shaking incubator at 37° C. for 30 minutes. The reaction was stopped and protein was precipitated by the addition of 5 parts of 2 N hydrochloric acid. The reaction mixture was extracted three times with 100 parts of diethyl ether and after being dried over anhydrous sodium sulphate the extracts were evaporated to dryness at room temperature in a current of air. The 5,7-dihydroxy-6,7,8,9-tetrahydro-4-oxo-10-propyl-4H-naphtho[2,3-b]pyran-2-carboxylic acid and the other dihydroxy compounds identified in Example 1 were isolated by the preparative layer chromatography technique described in Example 1.

EXAMPLE 3

6-Hydroxy-6,7,8,9-tetrahydro-4-oxo-10-propyl-4H-naphtho-[2,3-b]-pyran-2-carboxylic acid 7-Hydroxy-6,7,8,9-tetrahydro-4-oxo-10-propyl-4H-naphtho[2,3-b]-pyran-2-carboxylic acid 8-Hydroxy-6,7,8,9-tetrahydro-4-oxo-10-propyl-4H-naphtho-[2,3-b]-pyran-2-carboxylic acid 9-Hydroxy-6,7,8,9-tetrahydro-4-oxo-10-propyl-4H-naphtho-[2,3-b]-pyran-2-carboxylic acid The title compounds were made using the techniques of Examples 1 and 2, but substituting 6,7,8,9-tetrahydro-4-oxo-10-propyl-4H-naphtho-[2,3-b]pyran-2-carboxylic acid sodium salt for the 6,7,8,9-tetrahydro-5-hydroxy-4-oxo-10-propyl-4H-naphtho-[2,3-b]pyran-2-carboxylic acid sodium salt. the product compounds were identified and characterised by gas liquid chromatographic nuclear magnetic resonnance spectrometry and other analytical techniques.

EXAMPLE 4

(a) Methyl 6,7,8,9-tetrahydro-5-methoxy-4,6-dioxo-10-propyl-4H-naphtho[2,3-b]pyran-2-carboxylate I Methyl 6,7,8,9-tetrahydro-5-methoxy-4,9-dioxo-10-propyl-4H-naphtho-[2,3-b]pyran-2-carboxylate II Methyl 6,7,8,9-tetrahydro-5-methoxy-4-oxo-10-propyl-4H-naphtho-[2,3-b]pyran-2-carboxylate (81.4 g; 0.25 mole) was dissolved in acetone (1 l) and stirred rapidly while adding a solution of chromium trioxide (220 g) in water (830 ml) and concentrated sulphuric acid (190 ml), adding at such a rate that the acetone refluxed gently. The mixture was then stirred at room temperature overnight, poured into water (1 l) and extracted into chloroform (3×). The organic fractions were combined, dried (sodium sulphate) and evaporated to give a yellow oil which was submitted to high pressure liquid chromatography (HPLC) to separate the components.

The title '6-oxo' compound (I) (7.1 g; 8.4%) was isolated as a peach coloured solid mp 139°–144°.

The title '9-oxo' compound (II) (1.3 g; 1.5%) was isolated as a pale yellow solid after one recrystallisation (of the material isolated from HPLC) from cyclohexane mp 92°–5°.

(b) Methyl 6,7,8,9-tetrahydro-5-hydroxy-4,6-dioxo-10-propyl-4H-naphtho[2,3-b]pyran-2-carboxylate (III)

Methyl 6,7,8,9-tetrahydro-5-methoxy-4,6-dioxo-10-propyl-4H-naphtho[2,3-b]pyran-2-carboxylate (172 mg; 0.5 mmole) in formic acid (5 ml) was heated on a steam bath with ground potassium iodide (800 mg; 4.8 mmole) for 1 hour. The mixture was poured into water and extracted with ethylacetate (3×). The organic fractions were washed with water and dried (sodium sulphate) to yield a brown oil (180 mg) which crystallised on trituration with ethanol. The solid was filtered off and washed with a little ether to give the title compound as a yellow powder (110 mg; 67%) mp 200° (decomposition).

(c)
6,7,8,9-Tetrahydro-5-hydroxy-4,6-dioxo-10-propyl-4H-naphtho-[2,3-b]pyran-2-carboxylic acid The product from step (b) (200 mg; 0.61 mmole) in potassium hydroxide dried pyridine (5 ml) was heated on a steam bath with anhydrous lithium iodide (1 g; 7.5 mmole) for 1 hour. The mixture was cooled and concentrated hydrochloric acid diluted with an equal volume of water was added until the resulting suspension was at pH2. The product was extracted with ethylacetate, washed with water and dried (anhydrous sodium sulphate) to yield a red solid which was recrystallised from ethanol to give the title compound as red crystals (160 mg; 80%) mp 244° (decomposition).

(d)
6,7,8,9-Tetrahydro-5,6-dihydroxy-4-oxo-10-propyl-4H-naphtho-[2,3-b]pyran-2-carboxylic acid 6,7,8,9-Tetrahydro-5-hydroxy-4,6-dioxo-10-propyl-4H-naphtho-[2,3-b]pyran-2-carboxylic acid (158 mg; 0.5 mmole) was dissolved in 10 ml of a pH10 buffer made from sodium bicarbonate (0.65 g) sodium carbonate (1.32 g) in water (100 ml). Sodium borohydride (20 mg; 0.53 mmole=2.12 equivalents) was added and the solution was stirred for 1 hour at room temperature and then poured into dilute hydrochloric acid and the yellow solid was filtered off, washed with water and dried in a vacuum oven over phosphoric oxide to yield a pure sample of the title compound (120 mg; 75.5%) mp 245°-9°.

Mass spectrum shows M+ at 300, base peak 271. (e) By a similar procedure to that described in paragraphs (b), (c) and (d) above, 6,7,8,9-tetrahydro-5,9-dihydroxy-4-oxo-10-propyl-4H-naphtho[2,3-b]pyran-2-carboxylic acid was prepared.

EXAMPLE A

Erythrocyte Lysis Test (for assessment of membrane damaging properties of drugs)

Erythrocytes are prepared by centrifugation (2,500×g for 10 min) of freshly drawn heparinised rat blood. The separated erythrocytes are washed two times by resuspension in isotonic saline and recentrifugation. The erythrocytes are suspended in a volume equal to twice that of the original blood volume.

Centrifuge tubes containing solutions (0.95 ml) of the compound under test at the various concentrations to be tested in isotonic saline are incubated at 37° C. for 5 minutes. An aliquot (0.05 ml) of the erythrocyte suspension described above is then added and rapidly mixed. Incubations of the erythrocytes and test compound are performed at 37° C. for 15 minutes. Incubations are terminated by centrifugation of the tubes (2,500×g for 10 min) and removal of an aliquot (0.1 ml) of the resultant supernatant. The supernatant aliquot is diluted with distilled water to a final volume of 1 ml and the absorption measured at 416 nm in a spectrophotometer. Reference samples which allow quantitation of lytic ability are determined at the same time. These are produced by suspension of the erythrocytes in isotonic saline with no drug (0% lysis) and in distilled water (100% lysis).

This test gives a reliable indication of the ability of a compound to disrupt cell membranes. Thus the higher the concentration of compound required to disrupt a given proportion of the erythrocytes the less toxic the compound is.

I claim:
1. A compound of formula I,

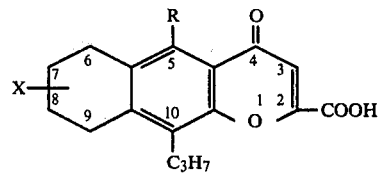

in which R is hydrogen, hydroxy, or alkoxy C 1 to 6, and
X is hydroxy, carbonyl oxygen or alkoxy C 1 to 6, and pharmaceutically acceptable salts, esters and amides thereof.

2. A compound according to claim 1, wherein X is —OH.

3. A compound according to claim 2, wherein R is —OH.

4. A compound according to claim 1, wherein —X is in the 7 position.

5. A compound according to claim 2 which is 5,7-Dihydroxy-6,7,8,9-tetrahydro-4-oxo-10-propyl-4H-naphtho[2,3-b]pyran-2-carboxylic acid.

6. A compound according to claim 1 and selected from 5,6-Dihydroxy-6,7,8,9-tetrahydro-4-oxo-10-propyl-4H-naphtho-[2,3-b]-pyran-2-carboxylic acid,
5,8-Dihydroxy-6,7,8,9-tetrahydro-4-oxo-10-propyl-4H-naphtho-[2,3-b]pyran-2-carboxylic acid,
5,9-Dihydroxy-6,7,8,9-tetrahydro-4-oxo-10-propyl-4H-naphtho-[2,3-b]pyran-2-carboxylic acid,
6-Hydroxy-6,7,8,9-tetrahydro-4-oxo-10-propyl-4H-naphtho-[2,3-b]pyran-2-carboxylic acid,
7-Hydroxy-6,7,8,9-tetrahydro-4-oxo-10-propyl-4H-naphtho-[2,3-b]pyran-2-carboxylic acid,
8-Hydroxy-6,7,8,9-tetrahydro-4-oxo-10-propyl-4H-naphtho-[2,3-b]pyran-2-carboxylic acid,
9-Hydroxy-6,7,8,9-tetrahydro-4-oxo-10-propyl-4H-naphtho-[2,3-b]pyran-2-carboxylic acid,
Methyl 6,7,8,9-tetrahydro-5-methoxy-4,6-dioxo-10-propyl-4H-naphtho[2,3-b]pyran-2-carboxylate,
Methyl 6,7,8,9-tetrahydro-5-methoxy-4,9-dioxo-10-propyl-4H-naphtho-[2,3-b]pyran-2-carboxylate,
Methyl 6,7,8,9-tetrahydro-5-hydroxy-4,6-dioxo-10-propyl-4H-naphtho[2,3-b]pyran-2-carboxylate,
6,7,8,9-Tetrahydro-5-hydroxy-4,6-dioxo-10-propyl-4H-naphtho-[2,3-b]pyran-2-carboxylic acid, and
6,7,8,9-Tetrahydro-5,9-dihydroxy-4-oxo-10-propyl-4H-naphtho[2,3-b]pyran-2-carboxylic acid.

7. A pharmaceutical composition for treatment of a condition involving the combination of antibody and specific antigen or involving skin mast cells or a delayed hypersensitivity reaction, said composition comprising an effective amount of a compound according to claim 2, as active ingredient, in combination with a pharmaceutically acceptable diluent, carrier or adjuvant.

8. A composition according to claim 7 comprising from 0.17 mg to 600 mg of active ingredient in unit dosage form.

9. A method of treatment of a condition involving the combination of antibody and specific antigen or involving skin mast cells or a delayed hypersensitivity reaction, which comprises administration of an effective amount of a compound according to claim 1 to a patient suffering from such a condition.

10. A compound of formula I,

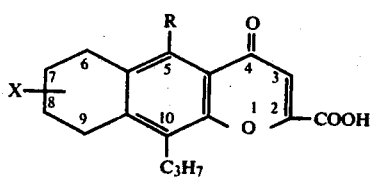
in which R is hydrogen, hydroxy, or alkoxy C 1 to 6, and
X is hydroxy or alkoxy C 1 to 6 in any of positions 6 to 9, or X is carbonyl oxygen in either of positions 6 or 9,
and pharmaceutically acceptable salts, esters and amides thereof.
* * * * *